United States Patent
Balducci et al.

(10) Patent No.: US 6,288,004 B1
(45) Date of Patent: Sep. 11, 2001

(54) ACTIVATION METHOD OF TITANIUM SILICALITE

(75) Inventors: Luigi Balducci, Mortara; Raffaele Ungarelli, Trecate; Daniele Bianchi, Arese; Maria Angela Mantegazza, Monza; Roberto Bagatin, Legnano, all of (IT)

(73) Assignees: Enichem S.p.A., S. Donato Mil.se; ENI S.p.A., Roma, both of (IT)

( * ) Notice: Subject to any disclaimer, the term of this patent is extended or adjusted under 35 U.S.C. 154(b) by 0 days.

(21) Appl. No.: 09/305,281

(22) Filed: May 5, 1999

(30) Foreign Application Priority Data

May 19, 1998 (IT) .............................. MI98A1087
Dec. 17, 1998 (IT) .............................. MI98A2712

(51) Int. Cl.$^7$ .............................. B01J 29/89; B01J 29/90
(52) U.S. Cl. .............................. 502/85; 502/64; 502/22
(58) Field of Search .............................. 502/22, 60, 64, 502/85

(56) References Cited

U.S. PATENT DOCUMENTS

| | | |
|---|---|---|
| 4,892,720 | 1/1990 | Skeels et al. . |
| 5,233,097 | 8/1993 | Nemeth et al. . |
| 5,254,746 | 10/1993 | Constantini et al. . |
| 5,688,484 | 11/1997 | Saxton et al. . |
| 5,906,954 | * 5/1999 | Koermer .............................. 502/60 |
| 5,977,009 | * 11/1999 | Faraj .............................. 502/64 |
| 6,063,944 | * 5/2000 | Di Renzo et al. .............................. 549/531 |
| 6,066,750 | * 5/2000 | Chang .............................. 549/524 |
| 6,087,514 | * 7/2000 | Thangaraj et al. .............................. 549/531 |

FOREIGN PATENT DOCUMENTS 0 267 362   5/1988   (EP) .

OTHER PUBLICATIONS

M.G. Clerici, et al., Journal of Catalysis, vol. 140, No. 1, pp. 71–83, "Epoxidation of Lower Olefins with Hydrogen Peroxide and Titanium Silicalite," Mar. 1, 1993.

* cited by examiner

Primary Examiner—Steven P. Griffin
Assistant Examiner—Christina Ildebrando
(74) Attorney, Agent, or Firm—Oblon, Spivak, McClelland, Maier & Neustadt, P.C.

(57) ABSTRACT

A method is described for improving the catalytic performances of titanium silicalite having formula (I) by the activation of the catalyst (I) in an aqueous medium with hydrogen peroxide, in the presence of precursors of fluoride ions or anionic species containing fluorine. The activated catalyst (I) is particularly useful in oxidation processes with hydrogen peroxide of organic substrates and, in particular, in hydroxylation reactions of aromatic compounds, amoximation reactions of carbonyl compounds, epoxidation reactions of olefinic compounds and oxidation reactions of nitrogenated compounds.

14 Claims, 1 Drawing Sheet

ACTIVATION METHOD OF TITANIUM SILICALITE

Figure 1:
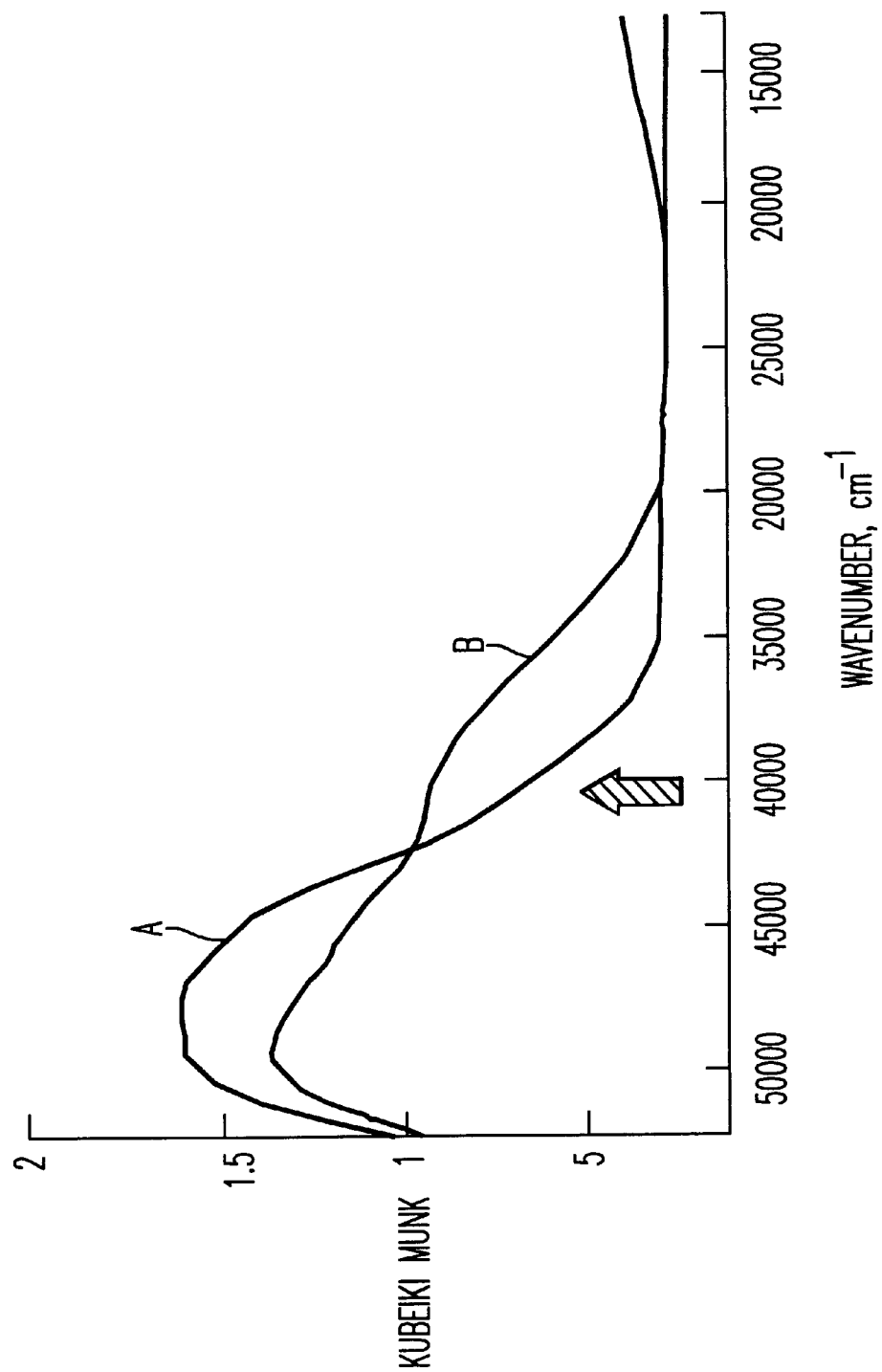

The present invention relates to a method for improving the catalytic performances of titanium silicalite having general formula (I) and its use in oxidation processes of organic substrates and the amoximation of carbonyl compounds with hydrogen peroxide.

It is known in literature that zeolite compounds with an MFI structure containing titanium (TS-1) are used as catalysts in direct oxidation reactions with hydrogen peroxide of substrates such as aromatic hydrocarbons (U.S. Pat. No. 4,369,783), olefins (EP-100,119), nitrogenated compounds (secondary amines U.S Pat. No. 4,918,194, ammonia U.S Pat. No. 5,320,819) and in amoximation reactions of carbonyl compounds (U.S Pat. No. 4,794,198, EP-496,385).

It is also known in literature that the catalytic performances of zeolite compounds in reactions with hydrogen peroxide can be effectively improved by subjecting these catalysts to suitable activation treatment.

For example the patent EP-230,949 describes a process for the preparation of epoxides from olefins and hydrogen peroxide which uses, as catalyst, a titanium silicalite treated, before or during the epoxidation reaction, with a neutralizing agent.

Among neutralizing agents the European patent discloses the use of organic derivatives of silicon of the X—Si(R)$_3$ type or hydrosoluble substances deriving from cations of group I or II with varying basic strength.

This process, however, has various limitations deriving, for example, from the reactivity of the organic compounds of silicon. A washing phase is consequently required after the treatment to remove the excess silanizer from the catalyst which, if it is not quantitative, can cause undesired reactions in the epoxidation phase, with the solvents and products formed in the reaction.

As far as the use of basic substances of cations of group I and II is concerned, a limitation derives from their hydrosolubility, making it necessary for a quantity of water to be present in the reaction solvent, right from the beginning, which completely dissolves them, if the neutralization treatment is carried out during the reaction.

U.S. Pat. No. 4,794,198 discloses an amoximation process of carbonyl compounds, in particular cyclohexanone, to the corresponding oximes which uses a titanium silicalite (TS-1) pretreated with aqueous solutions of hydrogen peroxide and/or in the presence of at least 0.5 equivalents/liter of acids having a pKa$\leq$5 (preferably H$_2$SO$_4$, HCl, HNO$_3$, H$_3$PO$_4$).

Operating according to this process, however, a relatively low productivity, intended as quantity of oxime produced per hour, per weight unit of titanium, is obtained. The production of oximes with good yields therefore implies the necessity of operating with high contents of catalyst and long reaction times, which is disadvantageous from an economic point of view and with respect to separation and purification treatment of the end-products.

In addition, the catalysts activated with the methods described above are specific for each reaction.

It has now been found, according to the present invention, that the catalytic performances of titanium silicalite (TS-1) in the above reactions can be improved if these catalysts are subjected, before use, to an activation treatment in an aqueous medium with hydrogen peroxide, in the presence of fluoride ions or anionic species containing fluorine.

The higher activity and selectivity of the activated catalyst forms the main advantage of the process of the present invention. This in fact simplifies the recovery operations of the products and recycling of the reagents with positive effects on the economy of the process. In addition, the catalysts activated with the method of the present invention have a general validity for all reactions catalyzed by titanium silicalite (oxidation and amoximation).

In accordance with this, a first objective of the present invention relates to a method for improving the catalytic performances of titanium silicalite having formula (I) by the activation of the catalyst (I) in an aqueous medium with hydrogen peroxide, in the presence of precursors of fluoride ions or anionic species containing fluorine.

A further object of the present invention relates to an oxidation process of organic substrates and an amoximation process of carbonyl compounds with hydrogen peroxide which uses, as catalyst, titanium silicalite having formula (I) activated in an aqueous medium with H$_2$O$_2$ in the presence of precursors of fluoride ions or anionic species containing fluorine.

The catalysts used in the process of the present invention are selected from those having general formula (I):

$$x\text{TiO}_2 \cdot (1-x)\text{SiO}_2 \qquad (I)$$

wherein x ranges from 0.0001 to 0.04.

The above titanium silicalites can be prepared according to the method described in U.S. Pat. No. 4,410,501 which also specifies their structural characteristics.

Alternatively these catalysts can be used in the form of microspheres with a high mechanical resistance prepared according to the processes described in U.S. Pat. Nos. 4,954,653 and 4,701,428.

It has been observed in fact that amorphous silica, used as ligand of submicronic particles of TS-1, does not jeopardize the effectiveness of the activation process of the catalyst.

Titanium silicalites in which part of the titanium is substituted by other metals such as boron, aluminum, iron and gallium, can also be used. These substituted titanium silicalites and the methods for their preparation are described in European patent applications 226,257, 226,258 and 266,825.

Examples of precursors of fluoride ions which can be used for the purposes of the present invention are selected from hydrofluoric acid, ammonium fluorides, fluorides of alkaline metals (NaF, KF, LiF, KHF$_2$) or of other metals soluble in water such as for example AlF$_3 \cdot$3H$_2$O.

In addition, inorganic fluoroderivatives soluble in water can be used in acid form such as for example fluosilicic acid (H$_2$SiF$_6$), fluoboric acid (HBF$_4$) and hexafluophosphoric acid (HPF$_6$), or in salified form for example with NH$_4$OH.

Among the fluorinated compounds mentioned above, ammonium derivatives are preferred, as the ammonium ion, optionally present as residue in the catalyst, can be more easily eliminated by thermal treatment at temperatures higher than 400° C. Ammonium fluoride and ammonium bifluoride (NH$_4$F, NH$_4$HF$_2$) are particularly preferred.

In order to control the pH of the reaction medium, the aqueous solutions of the fluorine compounds in acid form can be partially basified using for example NH$_4$OH.

The concentration of the fluorinated compound in the reaction medium is defined in relation to the concentration and composition of the titanium silicalite. Expressing the reagents in moles of F and Ti respectively, the molar ratio F/Ti can vary from 0.5 to 3.0. Under the preferred conditions in which NH$_4$F or H$_4$HF$_2$ are used, this ratio can range from 1.0 to 2.5.

Hydrogen peroxide in aqueous solution at 30–35% by weight is typically used in the activation reaction. The quantity of hydrogen peroxide is regulated in relation to the concentration of the titanium. Under the preferred conditions the molar ratio $H_2O_2/Ti$ is such as to range from 3.0 to 15, preferably from 6 to 12.

The combination of fluorinated compound/$H_2O_2$ is fundamental as the activation treatment without one of the two reagents is not very effective. The presence of hydrogen peroxide in the reaction system causes an increase in the solubilization degree of Ti (weight % of Ti removed from the titanium silicalite), whose control is a critical point of the activation process.

It has been observed in fact that, in relation to the chemical composition of the catalyst, the type and concentration of the fluorinated compound and the other reaction conditions (temperature and duration of the treatment), the quantity of Ti solubilized, referring to that originally present in the catalyst, can vary from 1 to 60% by weight.

Following the activation treatment, the UV-Vis spectrum of the TS-1 undergoes a modification, more or less distinct, consisting in the appearance of a new absorption band centered around 39,000 cm$^{-1}$. This modification can be seen in FIG. 1, which shows the UV-Vis spectra of the TS-1 of example 1 before (spectrum A) and after (spectrum B) the treatment.

Under the preferred activation conditions, in which ammonium fluoride or bifluoride and titanium silicalite with a high content of Ti (2.1–2.4% by weight of Ti) are used, a solubilization degree ranging from 30 to 50% produces highly selective and active catalysts.

Operating with catalysts having a smaller titanium content (1.5% by weight of Ti), catalytic performances analogous to those specified above are observed when the solubilization degree of Ti is higher than 10%.

The temperature and duration of the activation treatment of the catalyst are selected in relation to the solubilization degree of Ti desired.

The activation reaction is conveniently carried out at a temperature ranging from 20° C. to 100° C. It is preferable to operate within a temperature range of 60° C. to 90° C. with residence times, under constant temperature conditions, ranging from 1 to 6 hours.

The activation reaction of the catalyst can be carried out by initially preparing a suspension of the catalyst in an aqueous solution of the precursors of fluoride ions and hydrogen peroxide and subsequently thermostat-regulating this suspension to the selected temperature.

According to another embodiment of the method of the present invention, the hydrogen peroxide can be added to the aqueous suspension of the reagents previously thermostat-regulated to the reaction temperature.

At the end of the activation treatment, the catalyst is separated from the reaction medium and repeatedly washed with deionized water. The washing with water can be followed by a washing with solvents soluble in water and with a low boiling point, such as for example acetone, to remove the imbibition water of the material and facilitate its drying.

This operation, which is not critical, can be carried out under vacuum at temperatures lower than 100° C., or in air at 110–120° C. The catalyst after drying is calcined at temperatures ranging from 400° C. to 600° C., to ensure the complete removal of possibly adsorbable ions, such as for example the ammonium ion.

The catalysts obtained with the method of the present invention are active and selective in oxidation reactions of organic substrates and the amoximation of carbonyl compounds with hydrogen peroxide.

In particular, the activated catalysts can be advantageously used in hydroxylation reactions of aromatic compounds, amoximation reactions of carbonyl compounds, epoxidation reactions of olefinic compounds and oxidation reactions of nitrogenated compounds.

The quantity of catalyst used as well as the reaction conditions are selected in relation to the substrate to be oxidized.

Aromatic compounds which can be used in the process of the present invention can be selected, for example, from benzene, toluene, ethylbenzene, chlorobenzene and anisol. The hydroxylation reaction can be carried out as described for example in U.S. Pat. No. 4,369,783.

The hydroxylation of benzene to phenol with hydrogen peroxide is preferably carried out in the presence of solvents selected from the compounds having formula (II)

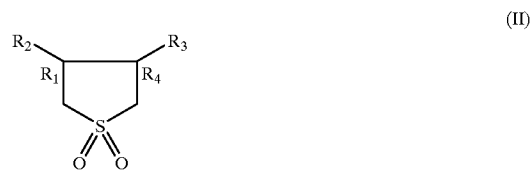

(II)

wherein: $R_1$, $R_2$, $R_3$ and $R_4$, the same or different, represent a hydrogen atom or an alkyl group with from 1 to 4 carbon atoms. In the compound having formula (II) $R_1$, $R_2$, $R_3$ and $R_4$ preferably represent a hydrogen atom.

It has been observed, in fact, that operating under these conditions, the inhibition is obtained of secondary reactions which cause the formation of dihydroxybenzenes such as catechol and hydroquinone, whereas the yield to phenol, intended as molar ratio between the hydroxylated compound produced and the aromatic substrate charged, remains in line with that obtained with the non-activated catalyst.

The activated catalyst is generally used in quantities ranging from 2 to 40% by weight with respect to the benzene. Preferably quantities of catalyst are used ranging from 5 to 15% by weight with respect to the benzene.

The hydrogen peroxide is added to the reaction mixture in quantities ranging from 5 to 50% in moles with respect to the aromatic substrate, preferably from 10 to 30% in moles.

Solutions of hydrogen peroxide at a concentration ranging from 1 to 60% by weight, preferably from 3 to 30% by weight, are conveniently used.

The aromatic substrate is used in quantities ranging from 10 to 80% by weight with respect to the reaction mixture. Quantities of aromatic substrate ranging from 30 to 60% by weight with respect to the reaction mixture, are preferably used.

The reaction time necessary for the complete use of the hydrogen peroxide depends on the reaction conditions used.

At the end of the hydroxylation reaction the reaction product is recovered together with the non-reacted substrate using the conventional techniques, such as for example fractionated distillation and crystallization.

The catalyst obtained with the method of the present invention is, furthermore, extremely active in the amoximation reaction of carbonyl compounds, in particular cyclohexanone, as it improves the productivity of the oxidated product. The amoximation reaction can be carried out as described in the patents U.S Pat. No. 4,794,198 and EP-496,385.

Examples of olefins which can be epoxidated with the process of the present invention are: ethylene, propylene, allyl chloride, allyl alcohol, butenes, pentenes, hexenes, mesityl oxide, isoprene, cyclooctene and cyclohexene. In particular the epoxidation of ethylene and propylene can be carried out as described, for example, in the patent EP-100,119.

Examples of nitrogenated compounds which can be oxidated with the catalyst activated with the method of the present invention can be selected from ammonia and secondary amines. The oxidation of these compounds can be carried out as described in the patents U.S. Pat. Nos. 5,320,819 and 4,918,194.

The catalyst activated with the method of the present invention can also be used in operations in continuous, without there being any significant deterioration in the activity and selectivity.

The following examples, whose sole purpose is to describe the present invention in greater detail, should in no way be considered as limiting the scope of the invention itself.

EXAMPLE 1

3.0 g (1.43 mmoles of Ti) of catalyst TS-1 (Eni-Chem, Ti=2.29% by weight) and 0.11 g of $NH_4HF_2$ (Fluka; average titer 92.5%) in 35 ml of water, corresponding to a molar ratio F/Ti=2.5, are charged into a glass flask having a capacity of 100 ml, equipped with a mechanical stirrer, reflux condenser, thermometer and oil circulation thermostat. The aqueous suspension of the catalyst, maintained under mechanical stirring, is heated to 60° C. 1.6 ml of $H_2O_2$ at 30% by weight (C. Erba; density 1.122 g/ml at 20° C.), equal to a molar ratio $H_2O_2$/Ti=11, are subsequently added and the suspension is maintained under stirring, at 60° C. for 4 hours. After cooling, the solid is separated from the mother liquor (pH 4.3) by filtration on a porous septum, and is then washed repeatedly with deionized water and finally with acetone. The catalyst is subsequently dried under vacuum at 40° C. for 8 hours and then subjected, with a heating rate of 50° C./h, to thermal treatment in air at 550° C. for 4 hours. The titer of the activated catalyst is 1.49% of Ti. The solubilized titanium corresponds to 35% by weight.

EXAMPLES 2–5

The same procedure is adopted as in example 1, but effecting the activation at 80° C. for 4 hours and with different ratios of the reagents. The results are indicated in Table 1.

TABLE 1

| | Molar ratio | | Ti (%) | Ti (%) |
|---|---|---|---|---|
| Example | F/Ti | $H_2O_2$/Ti | (a) | (b) |
| 2 | 2.5 | 11 | 1.15 | 50 |
| 3 | 1.1 | 11 | 1.65 | 28 |
| 4 | 2.5 | 6.9 | 1.36 | 40.8 |
| 5 | 1.75 | 6.9 | 1.33 | 41.9 |

(a) titer of the activated catalyst (Ti % by weight);
(b) % of solubilized Ti.

EXAMPLE 6

The reaction is carried out as described in example 1, but using 0.112 g of $NH_4F$ (Fluka; titer≧98%) corresponding to a molar ratio F/Ti=2.07. The aqueous suspension is heated to 80° C. and 1.6 ml of $H_2O_2$ at 30% by weight (equal to a molar ratio $H_2O_2$/Ti=11.0) are subsequently added. The suspension is maintained under stirring, at 80° C. for 4 hours and the procedure of example 1 is then followed. The titer of the catalyst is 1.57% of Ti. The solubilized titanium corresponds to 31.6%.

EXAMPLE 7

The same procedure is adopted as described in example 1, but using 0.55 g of $NH_4F$ in 35 ml of deionized water, corresponding to a molar ratio F/Ti=1.02. 1.6 ml of $H_2O_2$ at 30% by weight (molar ratio $H_2O_2$/Ti=11.0) are added to the suspension heated to 60° C.; the temperature is maintained at 60° C. for 4 hours and the procedure of example 1 is then followed. Titer of catalyst: 1.85% of Ti. The solubilized titanium corresponds to 19%.

EXAMPLE 8

The reaction is carried out as described in example 7, but using a molar ratio F/Ti=2.82. Titer of the activated catalyst= 1.85% of Ti. The solubilized titanium corresponds to 19%.

EXAMPLE 9

The same procedure is adopted as in example 1, but using a titanium-silicalite (TS-1, EniChem) with a titer equal to 2.11% of Ti. The activated catalyst has a Ti titer of 1.32%. The solubilized titanium corresponds to 37% by weight.

EXAMPLE 10

The same procedure is adopted as in example 6, but using a titanium-silicalite (TS-1, EniChem) with a titer equal to 2.11% of Ti. The titer of the activated catalyst is 1.34% of Ti. The solubilized titanium corresponds to 37% by weight.

EXAMPLE 11

The same procedure is adopted as in example 1, but using a titanium-silicalite (TS-1, EniChem) with a titer equal to 1.5% of Ti. Titer of the activated catalyst=1.29% of Ti. The solubilized titanium corresponds to 14% by weight.

EXAMPLE 12

The same procedure is adopted as in example 1, but using a solution of 0.72 mmoles of hydrofluoric acid (HF) corresponding to a molar ratio F/Ti=0.5. The same procedure is then followed as in example 1. The titer of the activated catalyst is equal to 1.72% of Ti. The solubilized titanium corresponds to 25% by weight.

EXAMPLE 13

3.0 g of TS-1 of example 1 (Ti=2.29% by weight) are suspended in a solution of 0.77 mmoles of fluoboric acid ($HBF_4$) corresponding to a molar ratio F/Ti=0.5. The solution is brought to pH 4.7 with a solution of $NH_4OH$. The same procedure is then followed as in example 1. The titer of the activated catalyst is 0.82% of Ti. The solubilized titanium corresponds to 64%.

EXAMPLE 14

The same procedure is used as in example 1, but using a solution of 0.159 mmoles of $AlF_3.3H_2O$ (Fluka, titer≧97%) corresponding to a molar ratio F/Ti=0.33. The titer of the activated catalyst is 2.23% of Ti. The solubilized titanium corresponds to 2.6%.

EXAMPLE 15

3.0 g of TS-1 of example 1 are suspended in a solution of 0.24 mmoles of hexafluosilicic acid ($H_2SiF_6$) in 35 ml of deionized water (molar ratio F/Ti=1.01). The same procedure is then followed as in example 1. The titer of the activated catalyst is 2.14% of Ti. The solubilized titanium corresponds to 6.4%.

EXAMPLE 16

12.9 g (5.68 mmoles of Ti) of catalyst TS-1 (Eni-Chem, Ti=2.11% by weight) and 0.23 g of $NH_4F$ in 140 ml of water, corresponding to a molar ratio F/Ti=1.09, are charged into a glass flask having a capacity of 100 ml, equipped with a mechanical stirrer, reflux condenser, thermometer and oil circulation thermostat.

The aqueous suspension of the catalyst is heated to 60° C. under mechanical stirring. 6.4 ml of $H_2O_2$ at 30% by weight equal to a molar ratio $H_2O_2$/Ti=11, are subsequently added and the suspension is maintained under stirring, at 60° C. for 4 hours.

After cooling, the solid is separated from the mother liquor (pH 4.3) by filtration on a porous septum, and is then washed repeatedly with deionized water and finally with acetone. The catalyst is subsequently dried under vacuum at 40° C. for 8 hours and then subjected, with a heating rate of 50° C./h, to thermal treatment in air at 550° C. for 4 hours. The activated catalyst has a Ti titer equal to 1.74% by weight. The solubilized titanium corresponds to 17.5% by weight.

EXAMPLE 17
Synthesis of Phenol from Benzene

The hydroxylation reaction of benzene is carried out using a glass reactor having a capacity of 30 ml, with a flat bottom, jacketed, equipped with a magnetic stirrer, feeding inlet of the reagents, temperature control and reflux condenser cooled to 0° C. with silicon oil circulation by thermocryostat. The solution of $H_2O_2$ is dosed with an appropriate graduated drip funnel equipped with a regulation valve.

7.04 g of benzene (titer 99.5% Fluka) (90 mmoles), 0.7 g of activated catalyst as described in example 1 (equal to 0.22 mmoles of Ti) and 15 g of sulfolane (Aldrich, titer 99%), are charged into the reactor maintained under a nitrogen atmosphere. The temperature of the mixture is brought to 80° C.

1.04 g (9 mmoles of $H_2O_2$) of an aqueous solution of $H_2O_2$ at 33% w/v, (Rudipont, Reagent Grade, density=1.11 at 20° C.) are subsequently added over a period of two hours.

After 15 minutes of conditioning at a constant temperature, under stirring, the reaction mixture is cooled to 20° C. The catalyst is separated by filtration on a glass porous septum under nitrogen pressure and washed repeatedly with acetonitrile (titer 99.9%, C. Erba Reagenti, RS).

The solution is analyzed by HPLC Shimadzu SCL-6A (LiChrospher 100 RP-18, 5 mm endcapped column, Merck thermostat-regulated at 40° C.), using acetonitrile and an aqueous solution of $H_3PO_4$ 0.01 M as eluants. Analysis of the reaction product gave the following results:

conversion of benzene (C1) 6.2% (in moles);
yield to phenol (Y1) 6.2% (in moles);
selectivity to phenol (S1) 100% (in moles);
hourly turnover (TOH)=9.52 (m/m Ti·h)

HPLC analysis did not reveal the formation of products different from phenol.

EXAMPLE 18 COMPARATIVE

The reaction is carried out under the same operating conditions as example 17, but using the same weight quantity of the corresponding non-activated catalyst.

Analysis of the reaction product gave the following results:

conversion of benzene (C1) 7.1% (in moles);
yield to phenol (Y1) 6.4% (in moles);
selectivity to phenol (S1) 90% (in moles);
hourly turnover (TOH)=7.49 (m/m Ti·h)

HPLC analysis revealed the formation of dihydroxylated products such as catechol and hydroquinone.

EXAMPLES 19–22

The reaction is carried out as described in example 17, but using the activated catalysts as in examples 2–5. The results are indicated in Table 2.

TABLE 2

| Examples<br>Catalyst | 19<br>Ex. 2 | 20<br>Ex. 3 | 21<br>Ex. 4 | 22<br>Ex. 5 |
|---|---|---|---|---|
| C1 (%) | 6 | 6.4 | 6 | 6 |
| Y1 (%) | 6 | 6.2 | 6 | 6 |
| S1 (%) | 100 | 97 | 100 | 100 |
| TOH (m/m Ti · h) | 15 | 10.3 | 11.91 | 12.57 |

EXAMPLES 23–25

The hydroxylation reaction of benzene is carried out under the operating conditions of example 17, but using the catalysts of examples 6, 7 and 8. The results are indicated in Table 3.

TABLE 3

| Example<br>Catalyst | 23<br>Ex. 6 | 24<br>Ex. 7 | 25<br>Ex. 8 |
|---|---|---|---|
| C1 (%) | 6.2 | 6.8 | 7.3 |
| Y1 (%) | 6.2 | 6.6 | 7.1 |
| S1 (%) | 100 | 97.2 | 96.7 |
| TOH (m/m Ti · h) | 10.8 | 9.83 | 10.49 |

EXAMPLE 26

The hydroxylation reaction of benzene is carried out under the operating conditions of example 17, but using the same weight quantity of the activated catalyst as in example 9.

The results are the following:

conversion of benzene (C1)=5.8% (in mmoles);
yield to phenol (Y1)=5.8% (in mmoles);
selectivity to phenol (S1)=100%;
TOH=11.01 (m/m Ti·h)

EXAMPLE 27 COMPARATIVE

The reaction is carried out under the same conditions as example 26, but using the same weight quantity of the corresponding non-activated catalyst (Ti=2.11%). The results are the following:

conversion of benzene (C1)=5.9% (in mmoles);
yield to phenol (Y1)=5.5% (in mmoles);
selectivity to phenol (S1)=93.8%;
TOH=6.51 (m/m Ti·h).

EXAMPLE 28

The reaction is carried out under the same operating conditions as example 17, but using the same weight quantity of the activated catalyst as in example 11.

The results are the following:
conversion of benzene (C1)=5.0% (in mmoles);
yield to phenol (Y1)=5.0% (in mmoles);
selectivity to phenol (S1)=100%;
TOH=10.43 (m/m Ti·h).

EXAMPLE 29

Comparative

The reaction is carried out as described in example 28, but using the same weight quantity of the corresponding non-activated catalyst (Ti=1.50%). The results are the following:
conversion of benzene (C1)=4.4% (in mmoles);
yield to phenol (Y1)=4.2% (in mmoles);
selectivity to phenol (S1)=95.7%;
TOH=7.68 (m/m Ti·h).

EXAMPLES 30–33

The hydroxylation reaction of benzene is carried out under the operating conditions of example 17, but using the catalysts of examples 12–15. The results are indicated in Table 4.

TABLE 4

| Examples Catalyst | 30 Ex. 12 | 31 Ex. 13 | 32 Ex. 14 | 33 Ex. 15 |
|---|---|---|---|---|
| C1 (%) | 5.2 | 6.5 | 6.1 | 5.7 |
| Y1 (%) | 5.2 | 6.1 | 5.8 | 5.4 |
| S1 (%) | 100 | 94.2 | 94.7 | 94.7 |
| TOH (m/m Ti · h) | 8.3 | 20.41 | 7.03 | 6.76 |

EXAMPLES 34–35

The same procedure is adopted as in example 17, but effecting the hydroxylation reaction in acetonitrile. The results are indicated in Table 5.

TABLE 5

| Ex. | C1 (%) | Y1 (%) | S1 (%) | By-products |
|---|---|---|---|---|
| 34 | 3.4 | 2.8 | 81.4 | catechol + hydroquinone |
| 35 (*) | 7.1 | 5.6 | 79.1 | catechol + hydroquinone |
| 17 | 6.2 | 6.2 | 100 | — |

(*) non-activated catalyst.

EXAMPLES 36–37

The reaction is carried out as described in example 17, but using an equimolecular quantity of phenol (90 mmoles) instead of benzene. The results are indicated in Table 6.

TABLE 6

| Example | C1 (%) | Y1 (%) | S1 (%) | By-products |
|---|---|---|---|---|
| 36 | 3.6 | 2.2 | 61.4 | Quinone |
| 37 (*) | 5 | 4.4 | 87 | Quinone |

(*) non-activated catalyst
Y1 conversion of phenol to dihydroxybenzenes (catechol + hydroquinone).

EXAMPLES 38–41 COMPARATIVE 3.25 g (1.43 mmoles) of TS-1 (titer 2.11% of Ti) are suspended in 35 ml of an 0.5 N solution of the following acids: HCl, $H_2SO_4$, $H_3PO_4$, $HNO_3$. After heating to 60° C. 1.6 ml of $H_2O_2$ at 30% by weight are added and the suspension is maintained under stirring, at 60° C. for 4 hours. After cooling, the solid is separated from the mother liquor (pH 4.3) by filtration on a porous septum, and is then washed repeatedly with deionized water and finally with acetone. The catalyst is subsequently dried under vacuum at 40° C. for 8 hours and then subjected, with a heating rate of 50° C./h, to thermal treatment in air at 550° C. for 4 hours.

The activated catalysts are used in the hydroxylation of benzene operating as described in example 17. The results are shown in Table 7, compared with those obtained using the catalyst activated with $NH_4HF_2$ of example 26 and the non-activated catalyst of ex. 27.

TABLE 7

| Ex. | Treatment | C1 (%) | Y1 (%) | S1 (%) | by-products |
|---|---|---|---|---|---|
| 38 | HCl | 6 | 5.6 | 94 | catechol + quinone |
| 39 | $H_2SO_4$ | 5.8 | 5.5 | 95 | catechol + quinone |
| 40 | $H_3PO_4$ | 6.5 | 6.1 | 94.4 | catechol + hydroquinone |
| 41 | $HNO_3$ | 6 | 5.7 | 95 | catechol + quinone |
| 26 | $NH_4HF_2$ | 5.8 | 5.8 | 100 | — |
| 27 | — | 5.9 | 5.5 | 93.8 | catechol + quinone |

The treatment with acids characterized by $pKa \leq 5$, did not have significant effects on the selectivity.

EXAMPLES 42–44

The reaction is carried out as described in example 26, but using different molar ratios $H_2O_2$/benzene. The results are indicated in Table 8.

TABLE 8

| Ex. | $H_2O_2$/benzene | C1 | Y1 | S1 | By-products |
|---|---|---|---|---|---|
| 42 | 0.15 | 8.7 | 8.6 | 98.8 | quinone |
| 43 | 0.2 | 11.5 | 11.2 | 97.8 | quinone |
| 44 | 0.3 | 14.8 | 14 | 95 | quinone + catechol |
| 26 (ref) | 0.1 | 5.8 | 5.8 | 100 | 0 |

EXAMPLES 45–47

Comparative

The reaction is carried out as described in example 27, but using different molar ratios $H_2O_2$/benzene. The results are indicated in Table 9.

TABLE 9

| Ex. | $H_2O_2$/benzene | C1 | Y1 | S1 | By-products |
|---|---|---|---|---|---|
| 45 | 0.15 | 9.4 | 8.6 | 92.1 | quinone + catechol |
| 46 | 0.2 | 11.4 | 10.3 | 90.5 | quinone + catechol |
| 47 | 0.3 | 14.8 | 13.2 | 89.2 | quinone + catechol |
| 27 (ref) | 0.1 | 5.9 | 5.5 | 93.8 | quinone + catechol + hydroquinone |

EXAMPLE 48

Amoximation of Cyclohexanone 0.610 g (corresponding to 0.17 mmoles of Ti) of activated catalyst as per example 9 (containing 1.32% of Ti), 25 ml of an aqueous solution of ammonia (15% by weight, 0.21 moles), 25 ml of terbutanol and 9.84 g (0.10 mmoles) of cyclohexanone are charged into a 100 ml glass reactor, equipped with a stirrer and heating jacket, previously filled with an inert gas (helium).

The suspension is brought to 78° C. and 11.7 g of an aqueous solution of hydrogen peroxide at 30.43% by weight are fed, under stirring, in 50 minutes. At the end of the reaction the suspension is filtered and the solution is analyzed by gas-chromatography.
The results indicate:
- conversion of cyclohexanone 97.5%
- yield to oxime 90.5%
- selectivity to oxime (with respect to the converted cyclohexanone) 92.9%
- yield with respect to hydrogen peroxide 86.6%
- hourly turnover of the catalyst of 635 (oxime moles/Ti·h moles).

EXAMPLE 49

Comparative

The reaction is carried out under the same operating conditions as example 48, but using 0.39 g (0.17 mmoles of Ti) of the corresponding non-activated catalyst (2.11% by weight of Ti) of example 9.

Analysis of the reaction product gave the following results:
- conversion of cyclohexanone 68.8% in moles
- selectivity to oxime 81.0%
- yield to oxime 55.7%
- yield with respect to hydrogen peroxide 52.4%
- hourly turnover 387 (oxime moles/Ti·h moles).

EXAMPLE 50

Comparative

The reaction is carried out under the same operating conditions as example 48, but using 0.59 g (0.17 mmoles of Ti) of a non-activated catalyst having a titanium titer (1.38% by weight) similar to that of the activated catalyst of example 9.

Analysis of the reaction product gave the following results:
- conversion of cyclohexanone 68.2% in moles
- selectivity to oxime 76.1%
- yield to oxime 51.9%
- yield with respect to hydrogen peroxide 49.4%
- hourly turnover 369 (oxime moles/Ti·h moles).

EXAMPLE 51

The reaction is carried out under the same operating conditions as example 48, but using 0.59 g (0.17 mmoles) of an activated catalyst as described in example 10 (Ti titer 1.34% by weight).

Analysis of the reaction product gave the following results:
- conversion of cyclohexanone 85.5% in moles
- selectivity to oxime 90.5%
- yield to oxime 77.5%
- yield with respect to hydrogen peroxide 71.4%
- hourly turnover 543 (oxime moles/Ti·h moles).

EXAMPLE 52

The reaction is carried out under the same operating conditions as example 48, but using a quantity equivalent to 0.17 mmoles of an activated catalyst as described in example 16 (Ti titer 1.74% by weight). Analysis of the reaction product gave the following results:
- conversion of cyclohexanone 73.8% in moles
- selectivity to oxime 85.7%
- yield to oxime 63.3%
- yield with respect to hydrogen peroxide 58.2%
- hourly turnover 436 (oxime moles/Ti·h moles).

EXAMPLE 53

Comparative

The reaction is carried out under the same operating conditions as example 48, but using a quantity equivalent to 0.17 mmoles of Ti of an activated catalyst as described in example 39. Analysis of the reaction product gave the following results:
- conversion of cyclohexanone 68.3% in moles
- selectivity to oxime 76.3%
- yield to oxime 52.2%
- yield with respect to hydrogen peroxide 50.0%
- hourly turnover 360 (oxime moles/Ti·h moles).

EXAMPLE 54

Epoxidation of Propylene 375 g of a mixture of methanol/water (weight ratio 50/1) and 2.71 g (0.75 mmoles of Ti) of activated catalyst as per example 9, are charged into a 1 liter glass reactor, containing a mechanical stirrer and heating jacket, and equipped so as to effect liquid sampling at preset times.

The reactor is stirred at 800 rpm, heated to 40° C. and pressurized with propylene at a pressure of 4 atms. 28.5 g of $H_2O_2$ at 48.5% by weight are added in about 30 seconds and the mixture is left to react for 150 minutes. The temperature is kept constant at 40° C. thanks to the external jacket of the reactor and an internal coil connected to a cryostat. The pressure is kept constant at 4 atm by reintegrating the propylene consumption. 90 minutes after the addition of the hydrogen peroxide, a sample of the reaction solution is taken and is analyzed by gaschromatography. A conversion of hydrogen peroxide of 94% is obtained together with a selectivity to propylene oxide equal to 89%.

EXAMPLE 55

Oxidation of Ammonia 0.762 g (corresponding to 0.21 mmoles of Ti) of an activated catalyst as described in example 9, 25 ml of aqueous ammonia (at 15% by weight) and 25 ml of t-butanol, are charged, in an inert atmosphere, into a 100 ml jacketed glass reactor equipped with a magnetic stirrer.

The suspension is brought to 70° C. and 1.18 g of an aqueous solution of $H_{22}O$ at 30.97% by weight are fed, under stirring, in 17 minutes. At the end of the reaction the suspension is filtered and a yield to hydroxylamine of 52.7% with respect to the $H_2O_2$ is determined. The hourly turnover of the catalyst is equal to 99 (hydroxylamine moles/Ti·h moles).

EXAMPLE 56

Comparative

The reaction is carried out under the same operating conditions as example 55, but using 0.48 g (equal to 0.21 mmoles of Ti) of the corresponding non-activated catalyst (2.11% of Ti) of example 9. At the end of the reaction a yield to hydroxylamine of 49.5% with respect to the $H_2O_2$, is obtained. The hourly turnover of the catalyst is equal to 88 (hydroxylamine moles/Ti·h moles).

What is claimed is:

1. A method for improving the catalytic performance of a titanium silicalite catalyst having general formula (I):

$$xTiO_2.(1-x)SiO_2 \qquad (I)$$

wherein x ranges from 0.0001 to 0.04, which comprises activating the catalyst (I) in an aqueous medium with hydrogen peroxide, in the presence of precursors of fluoride ions or anionic species containing fluorine.

2. The method according to claim 1, wherein the catalyst having formula (I) is in the form of microspheres.

3. The method according to claim 1, wherein in the catalyst having formula (I), part of the titanium is substituted by other metals selected from the group consisting of boron, aluminum, iron and gallium.

4. The method according to claim 1, wherein the precursors of fluoride ions are selected from the group consisting of hydrofluoric acid, an ammonium fluoride, a fluoride of an alkaline metal a fluoride of a metal soluble in water, an inorganic fluoroderivative compound soluble in water in acid form and an inorganic fluoroderivative compound soluble in water in salified form with $NH_4OH$.

5. The method according to claim 4, wherein the precursors of fluoride ions are ammonium fluoride and bifluoride.

6. The method according to claim 4, wherein said fluoride of an alkaline metal is selected from the group consisting of NaF, KF, LiF and $KHF_2$.

7. The method according to claim 1, wherein said fluoride of a metal soluble in water is $AlF_3.3H_2O$.

8. The method according to claim 1, wherein said inorganic fluoroderivative compound soluble in water in acid form is selected from the group consisting of fluorosilicic acid, fluoroboric acid, and hexafluorophosphoric acid.

9. The method according to claim 1, wherein the quantity of fluorinated compound is such as to give a molar ratio F/Ti ranging from 0.5 to 3.0.

10. The method according to claim 9, wherein the molar ratio F/Ti ranges from 1.0 to 2.5.

11. The method according to claim 1, wherein the quantity of hydrogen peroxide is such that the molar ratio $H_2O_2$/Ti ranges from 3.0 to 15.

12. The method according to claim 11, wherein the molar ratio $H_2O_2$/Ti ranges from 6 to 12.

13. The method according to claim 1, wherein the activation reaction is carried out at a temperature ranging from 20° C. to 100° C.

14. The method according to claim 13, wherein the temperature is selected between 60° C. and 90° C.

* * * * *